United States Patent
Higashiyama et al.

(10) Patent No.: US 11,173,122 B2
(45) Date of Patent: Nov. 16, 2021

(54) ADDITIVE COMPOSITION FOR ORALLY DISINTEGRATING TABLET

(71) Applicant: SAWAI PHARMACEUTICAL Co., Ltd., Osaka (JP)

(72) Inventors: Yoichi Higashiyama, Osaka (JP); Wataru Izui, Osaka (JP); Ayako Harada, Osaka (JP); Satoru Ogihara, Osaka (JP); Kenji Nozawa, Osaka (JP); Hiroaki Kikuoka, Osaka (JP)

(73) Assignee: SAWAI PHARMACEUTICAL Co., Ltd., Osaka (JP)

( * ) Notice: Subject to any disclaimer, the term of this patent is extended or adjusted under 35 U.S.C. 154(b) by 100 days.

(21) Appl. No.: 16/258,235

(22) Filed: Jan. 25, 2019

(65) Prior Publication Data

US 2019/0151247 A1    May 23, 2019

Related U.S. Application Data

(63) Continuation of application No. PCT/JP2017/026762, filed on Jul. 25, 2017.

(30) Foreign Application Priority Data

Jul. 27, 2016  (JP) .............................. JP2016-147515

(51) Int. Cl.
   *A61K 9/20*   (2006.01)
   *A61K 47/26*  (2006.01)
   *A61K 47/38*  (2006.01)
   *A61K 47/34*  (2017.01)
   *A61K 9/00*   (2006.01)
   *A61K 47/32*  (2006.01)

(52) U.S. Cl.
   CPC .......... *A61K 9/2054* (2013.01); *A61K 9/0056* (2013.01); *A61K 9/2018* (2013.01); *A61K 9/2027* (2013.01); *A61K 9/2095* (2013.01); *A61K 47/26* (2013.01); *A61K 47/32* (2013.01); *A61K 47/34* (2013.01); *A61K 47/38* (2013.01)

(58) Field of Classification Search
   None
   See application file for complete search history.

(56) References Cited

U.S. PATENT DOCUMENTS

| | | |
|---|---|---|
| 2007/0275058 A1 | 11/2007 | Tanaka et al. |
| 2009/0092672 A1 | 4/2009 | Venkatesh et al. |
| 2009/0117182 A1 | 5/2009 | Akutagawa et al. |
| 2009/0148524 A1 | 6/2009 | Higuchi et al. |
| 2010/0187706 A1 | 7/2010 | Maruyama |
| 2010/0286286 A1 | 11/2010 | Ikeda et al. |
| 2011/0021643 A1 | 1/2011 | Endo et al. |
| 2011/0053942 A1 | 3/2011 | Fujiwara et al. |
| 2012/0237602 A1* | 9/2012 | Ikeda .............. A61P 25/08 424/480 |
| 2013/0338238 A1 | 12/2013 | Maruyama et al. |
| 2015/0045452 A1 | 2/2015 | Hiramura et al. |
| 2015/0328163 A1 | 11/2015 | Gujjar et al. |
| 2016/0089338 A1 | 3/2016 | Kawano et al. |

FOREIGN PATENT DOCUMENTS

| | | |
|---|---|---|
| CN | 102006861 A | 4/2011 |
| CN | 102740893 A | 10/2012 |
| CN | 104367560 A | 2/2015 |
| JP | S57-53100 A | 11/1982 |
| JP | 2000-327701 A | 11/2000 |
| JP | 2009-515871 A | 4/2009 |
| JP | 2010-254756 A | 11/2010 |
| JP | 2012-51810 A | 3/2012 |
| JP | 2014-015459 A | 1/2014 |
| JP | WO2015053227 A1 * | 4/2015 |
| JP | 5753661 B2 | 5/2015 |
| WO | 2005/037254 A1 | 4/2005 |
| WO | 2007/055427 A1 | 5/2007 |
| WO | 2007/074856 A1 | 7/2007 |
| WO | 2009/066773 A1 | 5/2009 |
| WO | 2009/123102 A1 | 10/2009 |
| WO | 2010/119851 A1 | 10/2010 |
| WO | 2013/146917 A1 | 10/2013 |

(Continued)

OTHER PUBLICATIONS

F-Melt Brochure, accessed from http://www.fujichemical.co.jp/english/medical/medicine/f-melt/f-melt_brochure.pdf.*
Japanese Pharmacopeia 16th Edition excerpt, pp. 937-938, 2011.*
Shin-Etsu L-HPC, accessed from https://www.metolose.jp/en/pharmaceutical/l-hpc.html.*
Office Action dated May 21, 2019 for the corresponding Japanese patent application No. 2018-529889, with partial English machine translation.
English translation of Written Opinion of the International Search Authority dated Sep. 12, 2017 for the corresponding PCT application No. PCT/JP2017/026762. (the corresponding non-English document has been filed on Jan. 25, 2019.).

(Continued)

*Primary Examiner* — Robert A Wax
*Assistant Examiner* — Randeep Singh
(74) *Attorney, Agent, or Firm* — Hauptman Ham, LLP

(57) ABSTRACT

Provided is a novel additive for an orally disintegrating tablet which imparts a rapid disintegration property and a tablet hardness to the orally disintegrating tablet and a method for producing the same. An additive for an orally disintegrating tablet according to one embodiment of the present invention includes a D-mannitol, a low-substituted hydroxypropyl cellulose (excluding those having a mean particle size of 20 μm or less and a substitution degree of the hydroxypropoxy groups of 11%, having a mean particle size of 45 μm or less and a substitution degree of the hydroxypropoxy groups of 14% and having a mean particle size of 45 μm or less and a substitution degree of the hydroxypropoxy groups of 11% together with a 90% cumulated particle size of 100 μm or less), a crospovidone and a crystalline cellulose.

17 Claims, 10 Drawing Sheets

(56) References Cited

FOREIGN PATENT DOCUMENTS

| WO | 2014/189034 A1 | 11/2014 |
|---|---|---|
| WO | 2015/053227 A1 | 4/2015 |

OTHER PUBLICATIONS

English machine translation of Office Action dated Nov. 20, 2018 for the corresponding Japanese patent application No. 2018-529889 (the corresponding non-English document has been filed on Jan. 25, 2019.).
Written Opinion of the International Search Authority dated Sep. 12, 2017 for the PCT application No. PCT/JP2017/026762.
Office Action dated Nov. 20, 2018 for the corresponding Japanese patent application No. 2018-529889.
Kalyan K. Saripella et al., "A Quality by Experimental Design Approach to Assess the Effect of Formulation and Process Variables on the Extrusion and Spheronization of Drug-Loaded Pellets Containing Polyplasdone XL-10" AAPS PharmSciTech, Apr. 2016, 17(2), p. 368-379.
International Search Report (PCT/ISA/210) dated Sep. 12, 2017 for the PCT application No. PCT/JP2017/026762.
Examination Report issued for corresponding Indian Patent Application No. 201917007396 dated Nov. 3, 2020.
Written Opinion of the International Search Authority dated Nov. 21, 2017 for the PCT application No. PCT/JP2017/031863 (correspond to co-pending U.S. Appl. No. 16/294,114).
Taiwanese Office Action dated Jun. 29, 2018 for the corresponding Taiwan application No. 16/294,114 (correspond to co-pending U.S. Appl. No. 16/294,114), with partial English translation.
International Search Report (PCT/ISA/210) dated Nov. 21, 2017 for the PCT application No. PCT/JP2017/031863 (correspond to co-pending U.S. Appl. No. 16/294,114) with English translation.
English translation of Written Opinion of the International Search Authority dated Nov. 21, 2017 for the corresponding PCT application No. PCT/JP2017/031863 (correspond to co-pending U.S. Appl. No. 16/294,114).
Mare Nishiura, "Current Status and Formulation Design of Orally Disintegraitng Tablets in Hospital Preparations", Journal of Pharmaceutical Science and Technology, Japan, 2012, vol. 72, No. 1, p. 30-34, cited in the NPL No. 6 with partial English machine translation.
Japanese Office Action dated Aug. 27, 2019 for the corresponding Japanese patent application No. 2018-538405 (correspond to co-pending U.S. Appl. No. 16/294,114), with partial English machine translation.
"Ashland. ""Polyplasdone™ crospovidone superdisintegrants."" Retrieved online Feb. 3, 2020. Retrieved from <URL: https://www.ash I and.com/file sou reel Ash land/Industries/Pharmaceutical/Lin ks/PT R-09 7-Polyplasdone_crospovidone_as_a_Superdisintegrant. pdf>; pp. 1-4. (Year: 2020)".
Chemopharm. "Comprecel®". Retreived online Feb. 3, 2020; Retreived from <URL: http://www.chemopharma.com/product/comprecel/>; pp. 1-5. (Year 2020).
Examination Report issued for corresponding Indian Patent Application No. 201917011160 (correspond to co-pending U.S. Appl. No. 16/294,114) dated Nov. 2, 2020.
Notice of Hearing issued for corresponding Indian Patent Application No. 201917011160 (correspond to co-pending U.S. Appl. No. 16/294,114) dated Mar. 11, 2021.
Office Action issued for co-pending U.S. Appl. No. 16/294,114 dated Feb. 6, 2020.

* cited by examiner

FIG. 1

| | Example 1 | Comparative Example 1 | Comparative Example 2 | Comparative Example 3 | Comparative Example 4 | Comparative Example 5 |
|---|---|---|---|---|---|---|
| Tableting pressure 6kN Hardness (N) | 36 | 22 | 27 | 28 | 26 | 27 |
| Oral disintegration (sec) | 22 | 15 | 15 | 16 | 17 | 15 |
| Tableting pressure 9kN Hardness (N) | 62 | 35 | 43 | 46 | 45 | 41 |
| Oral disintegration (sec) | 22 | 5 | 18 | 16 | 18 | 18 |
| Tableting pressure 12kN Hardness (N) | 82 | 51 | 59 | 64 | 61 | 58 |
| Oral disintegration (sec) | 20 | 19 | 17 | 18 | 20 | 20 |

FIG. 2

| D-mannitol | | Example 1 | Comparative Example 6 | Comparative Example 7 |
|---|---|---|---|---|
| | | Mannit P | Pearlitol 100SD | Mannit Q |
| Tableting pressure 6kN | Hardness (N) | 36 | 88 | 90 |
| | Oral disintegration (sec) | 22 | 22 | 20 |
| Tableting pressure 9kN | Hardness (N) | 62 | 151 | 149 |
| | Oral disintegration (sec) | 22 | 29 | 26 |
| Tableting pressure 12kN | Hardness (N) | 82 | 195 | 195 |
| | Oral disintegration (sec) | 20 | 50 | 43 |

FIG. 3

| | | Example 2 | Example 3 | Example 4 | Comparative Example 8 | Comparative Example 9 |
|---|---|---|---|---|---|---|
| Tableting pressure 6kN | Hardness (N) | 30 | 41 | 33 | 49 | 41 |
| | Oral disintegration (sec) | 12 | 14 | 14 | 17 | 16 |
| Tableting pressure 9kN | Hardness (N) | 56 | 64 | 50 | 77 | 61 |
| | Oral disintegration (sec) | 10 | 19 | 15 | 23 | 24 |
| Tableting pressure 12kN | Hardness (N) | 75 | 84 | 66 | 98 | 78 |
| | Oral disintegration (sec) | 16 | 28 | 23 | 40 | 36 |

FIG. 4

|  |  | Example 2<br>L·C = 11.2 | Example 5<br>L·C = 11.3 | Example 6<br>L·C = 8.3 | Example 7<br>L·C = 8.2 | Example 8<br>L·C = 5.3 | Example 9<br>L·C = 5.2 |
|---|---|---|---|---|---|---|---|
| Tableting pressure 6kN | Hardness (N) | 30 | 31 | 28 | 27 | 27 | 28 |
|  | Oral disintegration (sec) | 12 | 13 | 10 | 10 | 9 | 9 |
| Tableting pressure 9kN | Hardness (N) | 56 | 59 | 51 | 50 | 49 | 53 |
|  | Oral disintegration (sec) | 10 | 13 | 12 | 13 | 11 | 10 |
| Tableting pressure 12kN | Hardness (N) | 75 | 77 | 70 | 72 | 68 | 64 |
|  | Oral disintegration (sec) | 16 | 23 | 14 | 16 | 11 | 12 |

FIG. 5

| | | Example 3 | Example 10 | Comparative Example 10 | Comparative Example 11 | Example 11 | Example 12 | Comparative Example 12 |
|---|---|---|---|---|---|---|---|---|
| Crystalline cellulose | | PH-101 | UF-711 | KG-1000 | KG-802 | PH-101 | PH-101 | PH-101 |
| Crospovidone | | CL-F | CL-F | CL-F | CL-F | CL-SF | CL-M | CL |
| Tabletting pressure 6kN | Hardness (N) | 27 | 28 | | | 33 | 32 | 26 |
| | Oral disintegration (sec) | 9 | 9 | | | 12 | 11 | 10 |
| Tabletting pressure 9kN | Hardness (N) | 49 | 49 | 65 | 57 | 60 | 57 | 42 |
| | Oral disintegration (sec) | 11 | 9 | 11 | 9 | 13 | 12 | 11 |
| Tabletting pressure 12kN | Hardness (N) | 68 | 67 | 88 | 70 | 79 | 78 | 58 |
| | Oral disintegration (sec) | 11 | 11 | 14 | 12 | 13 | 15 | 11 |

FIG. 6

|  | | Example 8 | Comparative Example 13 | Comparative Example 14 |
|---|---|---|---|---|
| Tableting pressure 6kN | Hardness (N) | 27 | | 15 |
| | Oral disintegration (sec) | 9 | | 8 |
| Tableting pressure 9kN | Hardness (N) | 49 | | 24 |
| | Oral disintegration (sec) | 11 | | 10 |
| Tableting pressure 12kN | Hardness (N) | 68 | | 27 |
| | Oral disintegration (sec) | 11 | | 11 |

FIG. 7

| Disintegrant | | Example 8<br>Crospovidone CL-F | Comparative Example 15<br>Partly pregelatinized starch PCS | Comparative Example 16<br>Carmellose NS300 |
|---|---|---|---|---|
| Tableting pressure 6kN | Hardness (N) | 27 | 25 | |
| | Oral disintegration (sec) | 9 | 11 | |
| Tableting pressure 9kN | Hardness (N) | 49 | 42 | 42 |
| | Oral disintegration (sec) | 11 | 15 | 12 |
| Tableting pressure 12kN | Hardness (N) | 68 | 55 | 57 |
| | Oral disintegration (sec) | 11 | 20 | 18 |

FIG. 8

| L-HPC | | Comparative Example 17 NBD-020 | Comparative Example 18 NBD-022 |
|---|---|---|---|
| Tableting pressure 6kN | Hardness (N) | 40 | 25 |
| | Oral disintegration (sec) | 33 | 11 |
| Tableting pressure 9kN | Hardness (N) | 60 | 35 |
| | Oral disintegration (sec) | 44 | 13 |
| Tableting pressure 12kN | Hardness (N) | 56 | 30 |
| | Oral disintegration (sec) | 59 | 15 |

FIG. 9

| Premix additive | | Example 12<br>Present application | Comparative<br>Example 19<br>GRANFILLER-D | Comparative<br>Example 20<br>Pharmaburst | Comparative<br>Example 21<br>Smart EX | Comparative<br>Example 22<br>Parteck ODT |
|---|---|---|---|---|---|---|
| Tableting pressure 6kN | Hardness (N) | 32 | 33 | 34 | 78 | 107 |
| | Oral disintegration (sec) | 11 | 10 | 11 | 42 | 88 |
| Tableting pressure 9kN | Hardness (N) | 57 | 53 | 51 | 111 | 183 |
| | Oral disintegration (sec) | 12 | 11 | 13 | 82 | 105 |
| Tableting pressure 12kN | Hardness (N) | 78 | 63 | 64 | 56 | 40 |
| | Oral disintegration (sec) | 15 | 11 | 15 | 27 | 60 |

FIG. 10

| Premix additive | | Example 8<br>Present application | Comparative<br>Example 19<br>GRANFILLER-D | Comparative<br>Example 20<br>Pharmaburst |
|---|---|---|---|---|
| Initial | Thickness (mm) | 3.71 | 3.78 | 4.18 |
| | Hardness (N) | 49 | 53 | 51 |
| 25°C 75%RH 1W | Thickness (mm)<br>(Difference value mm) | 3.86<br>(+0.15) | 4.2<br>(+0.42) | 5.5<br>(+1.32) |
| | Hardness (N) | 38 | 25 | 0 |
| | Reduction ratio<br>in the hardness (%) | 22.4 | 52.8 | 100.0 |

ADDITIVE COMPOSITION FOR ORALLY DISINTEGRATING TABLET

CROSS REFERENCE TO RELATED APPLICATIONS

This application is based upon and claims the benefit of priority from the prior Japanese Patent Application No. 2016-147515, filed on Jul. 27, 2016, and PCT Application No. PCT/JP2017/026762, filed on Jul. 25, 2017, the entire contents of which are incorporated herein by reference.

FIELD

The present invention relates to an additive for an orally disintegrating tablet and a method for producing an additive for an orally disintegrating tablet. Especially, the present invention relates to an additive for an orally disintegrating tablet which imparts a rapid disintegration property and a tablet hardness to an orally disintegrating tablet when added thereto and a method for producing an additive for an orally disintegrating tablet.

BACKGROUND

An orally disintegrating tablet is a solid formulation which disintegrates rapidly in the oral cavity and is capable of being taken with the aid of saliva in the mouth or a small quantity of water. As a result, there is an increasing demand for the orally disintegrating tablet which enables an easy intake by a patient. It is desirable that the orally disintegrating tablet disintegrates rapidly with the aid only of saliva in the mouse or a small quantity of water within a period around 30 seconds or a shorter period.

On the other hand, due to the manufacturability of an orally disintegrating tablet and handling by patients, the orally disintegrating tablet should have a certain hardness. Accordingly, the disintegration time and the hardness of the orally disintegrating tablet should be adjusted within certain ranges.

In order to adjust the disintegration time and the hardness of an orally disintegrating tablet, the types and the contents of additives to be added to the orally disintegrating tablet should be investigated in various ways. Since such an investigation of the types and the contents of the additives to be added is expected to involve an extremely large number of combinations, tremendous efforts and costs will be required. Accordingly, premix additives whose compositions are manipulated preliminarily are proposed.

For example, Japanese Patent Application Laid-Open No. 2014-015459 describes a method for producing a composite granulate comprising at least a granulation step in which a water dispersion comprising at least a low-substituted hydroxypropyl cellulose having a hydroxypropoxy group substitution degree of 5 to 16% by mass, a polyvinyl alcohol, a first sugar or sugar alcohol and water is added while conducting granulation of a second sugar or sugar alcohol. Japanese Patent Application Laid-Open No. 2014-015459 discloses a base for an orally disintegrating tablet using the method for production of a tablet described in Japanese Patent No. 5753661.

International Patent Publication No. 2013/146917 describes a method for producing a disintegrable particle composition comprising three components including a first disintegrant component consisting of an acid-type carboxymethyl cellulose, a second disintegrant component which is one or more components selected from crospovidone, croscarmellose sodium, carboxymethyl starch sodium, low-substituted hydroxypropyl celluloses, carboxymethyl cellulose calcium and an excipient, the production method comprising a first wet granulation step using any two components among said three components and a second wet granulation step using the granulate obtained in the first wet granulation step and one component which is the remainder of said three components, a production method further involving a microcrystalline cellulose as a fourth component, and a production method comprising a third step for mixing a microcrystalline cellulose with the granulate obtained in the second wet granulation step.

SUMMARY

The base for the orally disintegrating tablet of Japanese Patent Application Laid-Open No. 2014-015459 has a long oral disintegration time and is required to have a further rapid disintegration property. The disintegrable particle composition of International Patent Publication No. 2013/146917 is problematic because of a substantial increase of the thickness of the orally disintegrating tablet and a substantial reduction in the hardness when stored under a moistened condition.

An object of the present invention is to provide a novel additive for an orally disintegrating tablet which imparts a rapid disintegration property and a tablet hardness to the orally disintegrating tablet and a method for producing the same.

According to one embodiment of the present invention, an additive for an orally disintegrating tablet including a D-mannitol, a low-substituted hydroxypropyl cellulose (excluding those having a mean particle size of 20 µm or less and a substitution degree of the hydroxyperopoxy groups of 11%, having a mean particle size of 45 µm or less and a substitution degree of the hydroxypropoxy groups of 14% and having a mean particle size of 45 µm or less and a substitution degree of the hydroxypropoxy groups of 11% together with a 90% cumulated particle size of 100 µm or less), a crospovidone and a microcrystalline cellulose is provided.

In the additive for an orally disintegrating tablet, the D-mannitol may have a mean particle size of 50 µm or less.

In the additive for an orally disintegrating tablet, the crospovidone may have a mean particle size of 100 µm or less.

In the additive for an orally disintegrating tablet, the microcrystalline cellulose may have a bulk density of 0.22 g/cm$^3$ or more.

Also according to one embodiment of the present invention, an orally disintegrating tablet including an additive for an orally disintegrating tablet described in any of those mentioned above and a pharmaceutically active ingredient is provided.

Also according to one embodiment of the present invention, a method for producing an additive for an orally disintegrating tablet including dispersing a low-substituted hydroxypropyl cellulose (excluding those having a mean particle size of 20 µm or less and a substitution degree of the hydroxypropoxy groups of 11%, having a mean particle size of 45 µm or less and a substitution degree of the hydroxypropoxy groups of 14% and having a mean particle size of 45 µm or less and a substitution degree of the hydroxypropoxy groups of 11% together with a 90% cumulated particle size of 100 µm or less) in water to prepare a dispersion and performing a granulation while spraying the dispersion to a mixture containing a D-mannitol, a crospovidone and a microcrystalline cellulose is provided.

In the method for producing an additive for an orally disintegrating tablet, the D-mannitol may have a mean particle size of 50 μm or less.

In the method for producing an additive for an orally disintegrating tablet, the crospovidone may have a mean particle size of 100 μm or less.

In the method for producing an additive for an orally disintegrating tablet, the microcrystalline cellulose may have a bulk density of 0.22 g/cm$^3$ or more.

BRIEF DESCRIPTION OF DRAWINGS

FIG. 1 shows the results of the measurements of hardness and oral disintegration time of the orally disintegrating tablet according to one embodiment of the present invention under respective tableting pressures.

FIG. 2 shows the results of the measurements of hardness and oral disintegration time of the orally disintegrating tablet according to one embodiment of the present invention under respective tableting pressures.

FIG. 3 shows the results of the measurements of hardness and oral disintegration time of the orally disintegrating tablet according to one embodiment of the present invention under respective tableting pressures.

FIG. 4 shows the results of the measurements of hardness and oral disintegration time of the orally disintegrating tablet according to one embodiment of the present invention under respective tableting pressures.

FIG. 5 shows the results of the measurements of hardness and oral disintegration time of the orally disintegrating tablet according to one embodiment of the present invention under respective tableting pressures.

FIG. 6 shows the results of the measurements of hardness and oral disintegration time of the orally disintegrating tablet according to one embodiment of the present invention under respective tableting pressures.

FIG. 7 shows the results of the measurements of hardness and oral disintegration time of the orally disintegrating tablet according to one embodiment of the present invention under respective tableting pressures.

FIG. 8 shows the results of the measurements of hardness and oral disintegration time of the orally disintegrating tablet of Comparative Example under respective tableting pressures.

FIG. 9 shows the results of the measurements of hardness and oral disintegration time of the orally disintegrating tablet according to one embodiment of the present invention under respective tableting pressures.

FIG. 10 shows the results of the evaluation of the changes in thickness and hardness of the orally disintegrating tablet according to one embodiment of the present invention before and after storage.

DESCRIPTION OF EMBODIMENTS

The followings are the description concerning an additive for an orally disintegrating tablet according to the present invention and a method for producing the same. Nevertheless, the additive for an orally disintegrating tablet according to the present invention and the method for producing the same are not limited to the following embodiments or descriptions in Examples.

The additive for an orally disintegrating tablet according to the present invention, in one embodiment, includes D-mannitol, low-substituted hydroxypropyl celluloses, crospovidone, microcrystalline cellulose. However, from the low-substituted hydroxypropyl cellulose (hereinafter referred to also as L-HPC), those having a mean particle size of 20 μm or less and a substitution degree of the hydroxypropoxy groups of 11%, having a mean particle size of 45 μm or less and a substitution degree of the hydroxypropoxy groups of 14% and having a mean particle size of 45 μm or less and a substitution degree of the hydroxypropoxy groups of 11% together with a 90% cumulated particle size of 100 μm or less are excluded. The method for measuring the substitution degrees of the hydroxypropoxy group of the low-substituted hydroxypropyl cellulose employed here is based on Japanese Pharmacopoeia 16th Edition. The substitution degree is represented as a % by mass of the hydroxypropoxy group in a low-substituted hydroxypropyl cellulose. A low-substituted hydroxypropyl cellulose having a mean particle size of 20 μm or less and a substitution degree of the hydroxypropoxy groups of 11%, having a mean particle size of 45 μm or less and a substitution degree of the hydroxypropoxy groups of 14% and having a mean particle size of 45 μm or less and a substitution degree of the hydroxypropoxy groups of 11% together with a 90% cumulated particle size of 100 μm or less, when contained, results in a problematic prolongation of the oral disintegration time. The average particle size of the low-substituted hydroxypropyl cellulose is determined by a laser diffraction method known widely to those skilled in the art.

In an additive for an orally disintegrating tablet according to one embodiment of the present invention, the low-substituted hydroxypropyl cellulose preferably has a mean particle size of 45 μm or more and a substitution degree of the hydroxypropoxy groups of 11% or less.

Such a low-substituted hydroxypropyl cellulose can be selected from, but is not limited to, the group consisting for example of LH-11, LH-21, LH-22, LH-B1 and NBD-022 supplied from Shin-Etsu Chemical Co., Ltd. Each low-substituted hydroxypropyl cellulose has the physical characteristics shown in Table 1. NBD-022 is especially preferred because it maintains the hardness of an orally disintegrating tablet while achieving a rapid oral disintegration time within 20 seconds. In Table 1, the physical characteristics of LH-21, NBD-021 and NBD-020, which are employed as Comparative Examples described below, are indicated for reference.

TABLE 1

| | Particle appearance | Hydroxy-propoxy group (%) | Mean particle size (μm) | 90% cumulated particle size (μm) |
|---|---|---|---|---|
| LH-11 | Most fibrous | 11 | 55 | 175 |
| LH-21 | Moderately fibrous | 11 | 45 | 135 |
| LH-22 | Moderately fibrous | 8 | 45 | 135 |
| LH-B1 | Non fibrous | 11 | 55 | 125 |
| NBD-022 | Short fiber | 8 | 45 | 100 |
| LH-31 | Micronized | 11 | 20 | 70 |
| NBD-021 | Short fiber | 11 | 45 | 100 |
| NBD-020 | Short fiber | 14 | 45 | 100 |

The D-mannitol to be added to an additive for an orally disintegrating tablet according to the present invention is not limited particularly. In one embodiment, the D-mannitol preferably has a mean particle size of 50 μm or less. The D-mannitol having a mean particle size of 50 μm or less may for example be, but is not limited to, Mannit P supplied from Mitsubishi Shoji Foodtech Co., Ltd. The mean particle size of the D-mannitol is determined by a laser diffraction method known widely to those skilled in the art.

The crospovidone to be added to an additive for an orally disintegrating tablet according to the present invention preferably has a mean particle size of 100 μm or less, more preferably has a mean particle size of 50 μm or less. A crospovidone having a mean particle size of 100 μm or less is preferred because it allows a hardness required in an orally disintegrating tablet to be obtained more easily. The average particle size of the crospovidone is determined by a laser diffraction method known widely to those skilled in the art.

In one embodiment, the crospovidone may for example be selected from, but is not limited to, the group consisting of Kollidon CL-F, Kollidon CL-SF and Kollidon CL-M supplied from BASF. Each crospovidone has the physical characteristics are shown in Table 2. Kollidon CL-M is especially preferred because it maintains the hardness of an orally disintegrating tablet while achieving a rapid oral disintegration time.

TABLE 2

|       | Swelling pressure (kPa) | Particle size (μm) |
|-------|-------------------------|--------------------|
| CL    | 170                     | 110 to 130         |
| CL-F  | 30                      | 20 to 40           |
| CL-SF | 25                      | 10 to 30           |
| CL-M  | 70                      | 3 to 10            |

In one embodiment, the low-substituted hydroxypropyl cellulose and the crospovidone preferably have a content ratio of 11:2 to 5:3. A reduction in the low-substituted hydroxypropyl cellulose content within this range allows a rapid disintegration property to be achieved while achieving a reduced time period required for a fluidized bed granulation described below, which leads to an improved manufacturability.

The microcrystalline cellulose to be added to an additive for an orally disintegrating tablet according to the present invention has a bulk density of 0.22 g/cm$^3$ or more. Because a microcrystalline cellulose having a bulk density less than 0.22 g/cm$^3$ may undergo sticking under a low tableting pressure condition, a microcrystalline cellulose having a bulk density of 0.22 g/cm$^3$ or more is preferred. The bulk density of the microcrystalline cellulose can be determined by the bulk density measurement method described in the section of microcrystalline cellulose in Japanese Pharmacopoeia 16th Edition.

In one embodiment, the microcrystalline cellulose may for example be selected from, but is not limited to, a group consisting of UF-702, UF-711, PH-101, PH-101D, PH-102, PH-200, PH-301, PH-301D, PH-302, PH-F20JP supplied from Asahi Kasei Corporation. Each microcrystalline cellulose has the physical characteristics are shown in Table 3. UF-711 having a mean particle size of 50 μm and a bulk density of 0.22 g/cm$^3$ and PH-101 having a mean particle size of 50 μm and a bulk density of 0.29 g/cm$^3$ are especially preferred because they can maintain the hardness of an orally disintegrating tablet without causing sticking.

TABLE 3

| Grade | Mean particle size (μm) | Bulk density (g/cm$^3$) | Loss on drying (%) | Repose angle (degree) |
|-------|-------------------------|-------------------------|--------------------|----------------------|
| UF-702 | 90 | 0.29 | 2.0-6.0 | 34 |
| UF-711 | 50 | 0.22 | 2.0-6.0 | 42 |

TABLE 3-continued

| Grade | Mean particle size (μm) | Bulk density (g/cm$^3$) | Loss on drying (%) | Repose angle (degree) |
|-------|-------------------------|-------------------------|--------------------|----------------------|
| KG-802 | 50 | 0.21 | 2.0-6.0 | 49 |
| KG-1000 | 50 | 0.12 | 2.0-6.0 | 57 |
| PH-101 | 50 | 0.29 | 2.0-6.0 | 45 |
| PH-101D | 50 | 0.29 | 1.0-3.0 | 45 |
| PH-102 | 90 | 0.3 | 2.0-6.0 | 42 |
| PH-200 | 170 | 0.35 | 2.0-6.0 | 36 |
| PH-301 | 50 | 0.41 | 2.0-6.0 | 41 |
| PH-301D | 50 | 0.41 | 1.0-3.0 | 41 |
| PH-302 | 90 | 0.43 | 2.0-6.0 | 38 |
| PH-F20JP | 20 | 0.23 | 7.0 or less | 60 or more |

An additive for an orally disintegrating tablet according to the present invention can adjust the orally disintegrating tablet to have desired disintegration time and hardness via adjustment of the grades of the respective additives and the contents of the respective additives. The additive for an orally disintegrating tablet according to the present invention is a novel additive for an orally disintegrating tablet which imparts a rapid disintegration property and a tablet hardness to an orally disintegrating tablet.

An orally disintegrating tablet containing an additive for an orally disintegrating tablet according to the present invention and a pharmaceutically active ingredient can be produced. The pharmaceutically active ingredient is not limited particularly, and various pharmaceutically active ingredients can be used to produce the orally disintegrating tablet. The orally disintegrating tablet can be produced by mixing the additive for an orally disintegrating tablet according to the present invention, the pharmaceutically active ingredient and a lubricant followed by tableting. The lubricant is not limited particularly, and any known lubricant can be employed. The lubricant may for example be, but is not limited to, magnesium stearate, stearic acid, calcium stearate, light anhydrous silicic acid, sodium stearyl fumarate, talc, hydrogenated vegetable oils, microcrystalline wax, sucrose fatty acid ester, polyethylene glycol and the like.

The orally disintegrating tablet may additionally contain further additives, such as seasonings, flavoring agents, fluidizing agents, antistatic agents, surfactants, wetting agents, bulking agents, adsorbents, desiccants, antioxidants, preservatives (for example, antiseptics), buffers and the like. The orally disintegrating tablet can also be film-coated.

(Methods for Producing Additives for Orally Disintegrating Tablets)

An additive for an orally disintegrating tablet according to the present invention is produced preferably by a fluidized bed granulation. It is especially preferred to use a dispersion containing a low-substituted hydroxypropyl cellulose (excluding those having a mean particle size of 20 μm or less and a substitution degree of the hydroxyperopoxy groups of 11%, having a mean particle size of 45 μm or less and a substitution degree of the hydroxypropoxy groups of 14% and having a mean particle size of 45 μm or less and a substitution degree of the hydroxypropoxy groups of 11% together with a 90% cumulated particle size of 100 μm or less) as being dispersed in water to conduct the fluidized bed granulation. An agitation-kneading method is not preferred because the hardness of the orally disintegrating tablet is extremely reduced.

For example, a low-substituted hydroxypropyl cellulose (excluding those having a mean particle size of 20 μm or less and a substitution degree of the hydroxyperopoxy groups of 11%, having a mean particle size of 45 μm or less and a substitution degree of the hydroxypropoxy groups of 14% and having a mean particle size of 45 μm or less and a substitution degree of the hydroxypropoxy groups of 11% together with a 90% cumulated particle size of 100 μm or less) is dispersed in water (purified water) to prepare a dispersion. Fluidized bed granulation of the low-substituted hydroxypropyl cellulose as dispersed in ethanol is not preferred because it causes sticking. A D-mannitol, a crospovidone and a microcrystalline cellulose are mixed to obtain a mixture. To this mixture, the water dispersion of the low-substituted hydroxypropyl cellulose is sprayed while conducting the fluidized bed granulation, thereby producing an additive for an orally disintegrating tablet according to the present invention. It is also preferable in the additive for an orally disintegrating tablet according to the present invention to regulate the particle size by a sieve.

(Methods for Producing Orally Disintegrating Tablets)

An orally disintegrating tablet can be produced by mixing an additive for an orally disintegrating tablet according to the present invention, a pharmaceutically active ingredient and a lubricant followed by tableting. The other additives can also be added and mixed to produce an orally disintegrating tablet. The orally disintegrating tablet can also be film-coated by a known method.

As described above, the present invention provides a novel additive for an orally disintegrating tablet which imparts a rapid disintegration property and a tablet hardness to the orally disintegrating tablet and a method for producing the same.

EXAMPLE

Example 1

An orally disintegrating tablet was produced as Example 1 of the present invention. 55 g of NBD-022 supplied from Shin-Etsu Chemical Co., Ltd. as a low-substituted hydroxypropyl cellulose was dispersed in 745 ml of purified water to prepare a dispersion. Using a fluidized bed granulation device (manufactured by Powrex Corp., Model: MP-01), 385 g of Mannit P supplied from Mitsubishi Shoji Foodtech Co., Ltd. as a D-mannitol, 10 g of Kollidon CL-F supplied from BASF as a crospovidone, and 50 g of PH-101 supplied from Asahi Kasei Corporation as a microcrystalline cellulose were mixed to obtain a mixture. A fluidized bed granulation was conducted while spraying the dispersion to the resultant mixture. The resultant granulate was regulated in the particle size by sieve No. 22, whereby the orally disintegrating tablet of Example 1 was obtained. To the additive for an orally disintegrating tablet of Example 1, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Example 1 was obtained.

Comparative Example 1

In Comparative Example 1, a fluidized bed granulation was conducted while splaying a granulation liquid which was purified water to a mixture of the low-substituted hydroxypropyl cellulose, D-mannitol, crospovidone and microcrystalline cellulose, and otherwise similarly to Example 1, the orally disintegrating tablet of Comparative Example 1 was produced.

Comparative Example 2

In Comparative Example 2, a half quantity of the low-substituted hydroxypropyl cellulose to be added was dispersed in purified water to prepare a granulation liquid, a fluidized bed granulation was conducted while spraying the granulation liquid to a mixture of the remaining half quantity of the low-substituted hydroxypropyl cellulose, D-mannitol, crospovidone and microcrystalline cellulose, and otherwise similarly to Example 1, the orally disintegrating tablet of Comparative Example 2 was produced.

Comparative Example 3

In Comparative Example 3, a microcrystalline cellulose was dispersed in purified water to prepare a granulation liquid, a fluidized bed granulation was conducted while spraying the granulation liquid to a mixture of the low-substituted hydroxypropyl cellulose, D-mannitol and crospovidone, and otherwise similarly to Example 1, the orally disintegrating tablet of Comparative Example 3 was produced.

Comparative Example 4

In Comparative Example 4, a half quantity of the microcrystalline cellulose to be added was dispersed in purified water to prepare a granulation liquid, a fluidized bed granulation was conducted while spraying the granulation liquid to a mixture of a low-substituted hydroxypropyl cellulose, D-mannitol, crospovidone and the remaining half quantity of microcrystalline cellulose, and otherwise similarly to Example 1, the orally disintegrating tablet of Comparative Example 4 was produced.

Comparative Example 5

In Comparative Example 5, crospovidone was dispersed in purified water to prepare a granulation liquid, a fluidized bed granulation was conducted while spraying the granulation liquid to a mixture of the low-substituted hydroxypropyl cellulose, D-mannitol and microcrystalline cellulose, and otherwise similarly to Example 1, the orally disintegrating tablet of Comparative Example 5 was produced.

Using tableting pressures of 6 kN, 9 kN and 12 kN, the orally disintegrating tablets of Example 1 and Comparative Examples 1 to 5 were produced respectively.

(Hardness)

The orally disintegrating tablets of Example 1 and Comparative Examples 1 to 5 were subjected to a tablet hardness meter (DC-50, OKADA SEIKO CO., LTD.) to measure the hardness of the tablets, and the average of the measured values of three tablets was calculated.

(Oral Disintegration Time)

The orally disintegrating tablets of Example 1 and Comparative Examples 1 to 5 were subjected to a sensory evaluation to measure the oral disintegration times.

The orally disintegrating tablets of Example 1 and Comparative Examples 1 to 5 which had been tableted under three tableting pressures gave the results of the measurements of the hardness and the oral disintegration time under respective tableting pressures shown in FIG. 1. Based on the results shown in FIG. 1, the orally disintegrating tablet of Example 1 obtained by the fluidized bed granulation of the dispersion of the entire amount of the low-substituted hydroxypropyl cellulose acquired the hardness corresponding to the tableting pressures, indicating an excellent moldability.

(Investigation of Mannitol Grades)

The effects of the mannitol grades on an orally disintegrating tablet were investigated.

Comparative Example 6

In the additive for an orally disintegrating tablet of Comparative Example 6, the mannitol in the additive for an orally disintegrating tablet of Example 1 was changed to Pearlitol (Registered Trademark) 100SD supplied by ROQUETTE PHARMA, and by a method otherwise similar to that for the orally disintegrating tablet of Example 1, the orally disintegrating tablet of Comparative Example 6 was produced.

Comparative Example 7

In the additive for an orally disintegrating tablet of Comparative Example 7, the mannitol in the additive for an orally disintegrating tablet of Example 1 was changed to Mannit Q supplied by Mitsubishi Shoji Foodtech Co., Ltd., and by a method otherwise similar to that for the orally disintegrating tablet of Example 1, the orally disintegrating tablet of Comparative Example 7 was produced.

Using tableting pressures of 6 kN, 9 kN and 12 kN, the orally disintegrating tablets of Example 1 and Comparative Examples 6 to 7 were produced respectively. The orally disintegrating tablets of Example 1 and Comparative Examples 6 to 7 which had been tableted under three tableting pressures gave the results of the measurements of the hardness and the oral disintegration time under respective tableting pressures shown in FIG. 2. The results of the measurement shown in FIG. 2 are the averages of each 5 tablets. From FIG. 2, it was evident that the orally disintegrating tablet of Example 1 exhibited an excellent disintegrability even when the tableting pressure was increased. On the other hand, the orally disintegrating tablets of Comparative Examples 6 to 7 exhibited the oral disintegration times prolonged to 40 seconds or longer.

(Investigation of Low-Substituted Hydroxypropyl Celluloses Grades)

The effects of the low-substituted hydroxypropyl cellulose grades on an orally disintegrating tablet were investigated.

Example 2

By the method similar to that for the orally disintegrating tablet of Example 1, an orally disintegrating tablet of Example 2 of another lot was produced.

Example 3

In the additive for an orally disintegrating tablet of Example 3, the low-substituted hydroxypropyl cellulose in the additive for an orally disintegrating tablet of Example 1 was changed to LH-21 supplied by Shin-Etsu Chemical Co., Ltd., and by a method otherwise similar to that for the orally disintegrating tablet of Example 1, the orally disintegrating tablet of Example 3 was produced.

Example 4

In the additive for an orally disintegrating tablet of Example 4, the low-substituted hydroxypropyl cellulose in the additive for an orally disintegrating tablet of Example 1 was changed to LH-B1 supplied by Shin-Etsu Chemical Co., Ltd., and by a method otherwise similar to that for the orally disintegrating tablet of Example 1, the orally disintegrating tablet of Example 4 was produced.

Comparative Example 8

In the additive for an orally disintegrating tablet of Comparative Example 8, the low-substituted hydroxypropyl cellulose in the additive for an orally disintegrating tablet of Example 1 was changed to LH-31 supplied by Shin-Etsu Chemical Co., Ltd., and by a method otherwise similar to that for the orally disintegrating tablet of Example 1, the orally disintegrating tablet of Comparative Example 8 was produced.

Comparative Example 9

In the additive for an orally disintegrating tablet of Comparative Example 9, the low-substituted hydroxypropyl cellulose in the additive for an orally disintegrating tablet of Example 1 was changed to NBD-021 supplied by Shin-Etsu Chemical Co., Ltd., and by a method otherwise similar to that for the orally disintegrating tablet of Example 1, the orally disintegrating tablet of Comparative Example 9 was produced.

Using tableting pressures of 6 kN, 9 kN and 12 kN, the orally disintegrating tablets of Example 2 to 4 and Comparative Examples 8 to 9 were produced respectively. The orally disintegrating tablets of Example 2 to 4 and Comparative Examples 8 to 9 which had been tableted under three tableting pressures gave the results of the measurements of the hardness and the oral disintegration time under respective tableting pressures shown in 3. Based on the results shown in FIG. 3, the orally disintegrating tablet of Example 2 acquired the hardness corresponding to the tableting pressures and also exhibited the most excellent disintegrability. The orally disintegrating tablets of Example 3 and 4 also acquired the hardness corresponding to the tableting pressures and also exhibited excellent disintegrability. On the other hand, the orally disintegrating tablets of Comparative Examples 8 to 9 exhibited the oral disintegration times prolonged to longer than 30 seconds when using a tableting pressure of 12 kN.

At the dispersion concentration of this Example, LH-11 and LH-22 caused plugging of the spray nozzle of the fluidized bed granulation device, and it became evident that when using the low-substituted hydroxypropyl cellulose of these grades the dispersion concentration should be changed. It also became evident that NBD-020 was unsuccessful in tableting due to poor packing which was attributable to a too low bulk density.

(Investigation of Content Ratio of Low-Substituted Hydroxypropyl Cellulose and Crospovidone)

The effects of the content ratio of the low-substituted hydroxypropyl cellulose and the crospovidone on an orally disintegrating tablet were investigated.

Example 5

In the additive for an orally disintegrating tablet of Example 5, modifications were made to the additive for an orally disintegrating tablet of Example 1 to use 380 g of the D-mannitol and 55 g of the low-substituted hydroxypropyl cellulose and 15 g of the crospovidone so that the ratio of the low-substituted hydroxypropyl cellulose and the crospovidone became 11:3, and by a method otherwise similar to that for the orally disintegrating tablet of Example 1, the orally disintegrating tablet of Example 5 was produced.

Example 6

In the additive for an orally disintegrating tablet of Example 6, modifications were made to the additive for an orally disintegrating tablet of Example 1 to use 395 g of D-mannitol and 40 g of the low-substituted hydroxypropyl cellulose and 15 g of the crospovidone so that the ratio of the low-substituted hydroxypropyl cellulose and the crospovidone became 8:3, and by a method otherwise similar to that for the orally disintegrating tablet of Example 1, the orally disintegrating tablet of Example 6 was produced.

Example 7

In the additive for an orally disintegrating tablet of Example 7, modifications were made to the additive for an orally disintegrating tablet of Example 1 to use 400 g of the D-mannitol and 40 g of the low-substituted hydroxypropyl cellulose and 10 g of the crospovidone so that the ratio of the low-substituted hydroxypropyl cellulose and the crospovidone became 8:2, and by a method otherwise similar to that for the orally disintegrating tablet of Example 1, the orally disintegrating tablet of Example 7 was produced.

Example 8

In the additive for an orally disintegrating tablet of Example 8, modifications were made to the additive for an orally disintegrating tablet of Example 1 to use 410 g of the D-mannitol and 25 g of the low-substituted hydroxypropyl cellulose and 15 g of the crospovidone so that the ratio of the low-substituted hydroxypropyl cellulose and the crospovidone became 5:3, and by a method otherwise similar to that for the orally disintegrating tablet of Example 1, the orally disintegrating tablet of Example 8 was produced.

Example 9

In the additive for an orally disintegrating tablet of Example 9, modifications were made to the additive for an orally disintegrating tablet of Example 1 to use 415 g of the D-mannitol and 25 g of the low-substituted hydroxypropyl cellulose and 10 g of the crospovidone so that the ratio of the low-substituted hydroxypropyl cellulose and the crospovidone became 5:2, and by a method otherwise similar to that for the orally disintegrating tablet of Example 1, the orally disintegrating tablet of Example 9 was produced.

Using tableting pressures of 6 kN, 9 kN and 12 kN, the orally disintegrating tablets of Examples 2 and 5 to 9 were produced respectively. The orally disintegrating tablets of Examples 2 and 5 to 9 which had been tableted under three tableting pressures gave the results of the measurements of the hardness and the oral disintegration time under respective tableting pressures shown in FIG. 4. Based on the results shown in FIG. 4, it became evident that every orally disintegrating tablet was successful in obtaining a sufficient hardness and a rapid oral disintegration time of 30 seconds or less. It became also evident that a reduction in the content of the low-substituted hydroxypropyl cellulose relative to the crospovidone resulted in a shorter oral disintegration time. It became evident on the other hand that an increase in the content of the low-substituted hydroxypropyl cellulose relative to the crospovidone resulted in an increased hardness. The orally disintegrating tablets according to the present invention can adjust the oral disintegration time and the hardness arbitrarily via adjustment of the content of the low-substituted hydroxypropyl cellulose relative to the crospovidone.

(Investigation of Microcrystalline Cellulose Grades)

The effects of the microcrystalline cellulose grades on an orally disintegrating tablet were investigated.

Example 10

In the additive for an orally disintegrating tablet of Example 10, the microcrystalline cellulose in the additive for an orally disintegrating tablet of Example 8 was changed to UF-711 supplied by Asahi Kasei Corporation, and by a method otherwise similar to that for the orally disintegrating tablet of Example 8, the orally disintegrating tablet of Example 10 was produced.

Comparative Example 10

In the additive for an orally disintegrating tablet of Comparative Example 10, the microcrystalline cellulose in the additive for an orally disintegrating tablet of Example 8 was changed to KG-1000 supplied by Asahi Kasei Corporation, and by a method otherwise similar to that for the orally disintegrating tablet of Example 8, the orally disintegrating tablet of Comparative Example 10 was produced.

Comparative Example 11

In the additive for an orally disintegrating tablet of Comparative Example 11, the microcrystalline cellulose in the additive for an orally disintegrating tablet of Example 8 was changed to KG-802 supplied by Asahi Kasei Corporation, and by a method otherwise similar to that for the orally disintegrating tablet of Example 8, the orally disintegrating tablet of Comparative Example 11 was produced.

Using tableting pressures of 6 kN, 9 kN and 12 kN, the orally disintegrating tablets of Examples 8 and 10 and Comparative Examples 10 to 11 were produced respectively. The orally disintegrating tablets of Examples 8 and 10 and Comparative Examples 10 to 11 which had been tableted under three tableting pressures gave the results of the measurements of the hardness and the oral disintegration time under respective tableting pressures shown in FIG. 5. The results of the measurement shown in FIG. 5 are the averages of each 5 tablets. Based on the results shown in FIG. 5, it was evident that the orally disintegrating tablets of Examples 8 and 10 achieved a sufficient hardness. However, the orally disintegrating tablets of Comparative Examples 10 to 11 underwent sticking when tableted under 6 kN, and it became also evident that the fluidability before tableting was poor.

(Investigation of Crospovidone Grades)

The effects of the crospovidone grades on an orally disintegrating tablet were investigated.

Example 11

In the additive for an orally disintegrating tablet of Example 11, the crospovidone in the additive for an orally disintegrating tablet of Example 8 was changed to Kollidon CL-SF supplied by BASF, and by a method otherwise similar to that for the orally disintegrating tablet of Example 8, the orally disintegrating tablet of Example 11 was produced.

Example 12

In the additive for an orally disintegrating tablet of Example 12, the crospovidone in the additive for an orally disintegrating tablet of Example 8 was changed to Kollidon CL-M supplied by BASF, and by a method otherwise similar to that for the orally disintegrating tablet of Example 8, the orally disintegrating tablet of Example 12 was produced.

Comparative Example 12

In the additive for an orally disintegrating tablet of Comparative Example 12, the crospovidone in the additive for an orally disintegrating tablet of Example 8 was changed to Kollidon CL supplied by BASF, and by a method otherwise similar to that for the orally disintegrating tablet of Example 8, the orally disintegrating tablet of Comparative Example 12 was produced.

Using tableting pressures of 6 kN, 9 kN and 12 kN, the orally disintegrating tablets of Examples 8, 11 to 12 and Comparative Example 12 were produced respectively. The orally disintegrating tablets of Examples 8, 11 to 12 and Comparative Example 12 which had been tableted under three tableting pressures gave the results of the measurements of the hardness and the oral disintegration time under respective tableting pressures shown in FIG. 5. The results of the measurement shown in FIG. 5 are the averages of each 5 tablets. Based on the results shown in FIG. 5, it was evident that the orally disintegrating tablets of Examples 8, 11 to 12 achieved a sufficient hardness corresponding to the tableting pressures. However, the orally disintegrating tablets of Comparative Example 12 were unsuccessful in obtaining a sufficient hardness.

(Comparison of Production Methods)

Production methods other than the Examples described above were also investigated.

Comparative Example 13

In Comparative Example 13, ethanol was used as a part of the dispersion medium to obtain an orally disintegrating tablet. As a low-substituted hydroxypropyl cellulose, 25 g of NBD-022 supplied from Shin-Etsu Chemical Co., Ltd. was dispersed in 350 ml of a 8:2 mixture of ethanol: purified water to obtain a dispersion. Using a fluidized bed granulation device (manufactured by Powrex Corp., Model: MP-01), 410 g of Mannit P supplied from Mitsubishi Shoji Foodtech Co., Ltd. as a D-mannitol, 15 g of Kollidon CL-F supplied from BASF as a crospovidone, and 50 g of PH-101 supplied from Asahi Kasei Corporation as a microcrystalline cellulose were mixed to obtain a mixture. A fluidized bed granulation was conducted while spraying the dispersion to the resultant mixture. The resultant granulate was regulated in the particle size by sieve No. 22, whereby the orally disintegrating tablet of Comparative Example 13 was obtained. To the additive for an orally disintegrating tablet of Comparative Example 13, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 13 was obtained.

Comparative Example 14

By agitation-kneading, an additive for an orally disintegrating tablet of Comparative Example 14 was obtained.

Using tableting pressures of 6 kN, 9 kN and 12 kN, the orally disintegrating tablets of Example 8 and Comparative Examples 13 to 14 were produced respectively. The orally disintegrating tablets of Example 8 and Comparative Examples 13 to 14 which had been tableted under three tableting pressures gave the results of the measurements of the hardness and the oral disintegration time under respective tableting pressures shown in FIG. 6. From the measurement results shown in FIG. 6, it was evident that the orally disintegrating tablet of Example 8 was successful in obtaining a hardness corresponding to the tableting pressures. On the other hand, the additive for an orally disintegrating tablet of Comparative Example 13 was not successful in being tableted. The additive for an orally disintegrating tablet of Comparative Example 14 obtained by agitation-kneading was not successful in obtaining a sufficient hardness.

(Investigation of Disintegrants)

Disintegrants other than crospovidone were investigated.

Comparative Example 15

In Comparative Example 15, 25 g of NBD-022 supplied from Shin-Etsu Chemical Co., Ltd. as a low-substituted hydroxypropyl cellulose was dispersed in 350 ml of purified water to obtain a dispersion. Using a fluidized bed granulation device (manufactured by Powrex Corp., Model: MP-01), a fluidized bed granulation was conducted while spraying the dispersion to a mixture of 410 g of Mannit P supplied from Mitsubishi Shoji Foodtech Co., Ltd. as a D-mannitol, 15 g of a partly pregelatinized starch PCS supplied from Asahi Kasei Corporation as a disintegrant and 50 g of PH-101 supplied from Asahi Kasei Corporation as a microcrystalline cellulose. The resultant granulate was regulated in the particle size by sieve No. 22, whereby the orally disintegrating tablet of Comparative Example 15 was obtained. To the additive for an orally disintegrating tablet of Comparative Example 15, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 15 was obtained.

Comparative Example 16

In Comparative Example 16, 25 g of NBD-022 supplied from Shin-Etsu Chemical Co., Ltd. as a low-substituted hydroxypropyl cellulose was dispersed in 350 ml of purified water to obtain a dispersion. Using a fluidized bed granulation device (manufactured by Powrex Corp., Model: MP-01), a fluidized bed granulation was conducted while spraying the dispersion to a mixture of 410 g of Mannit P supplied from Mitsubishi Shoji Foodtech Co., Ltd. as a D-mannitol, 15 g of Carmellose NS300 supplied from GOTOKU CHEMICAL COMPANY LTD. NS300 as a disintegrant and 50 g of PH-101 supplied from Asahi Kasei Corporation as a microcrystalline cellulose. The resultant granulate was regulated in the particle size by sieve No. 22, whereby the orally disintegrating tablet of Comparative Example 16 was obtained. To the additive for an orally disintegrating tablet of Comparative Example 16, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 16 was obtained.

Using tableting pressures of 6 kN, 9 kN and 12 kN, the orally disintegrating tablets of Example 8 and Comparative Examples 15 to 16 were produced respectively. The orally disintegrating tablets of Example 8 and Comparative Examples 15 to 16 which had been tableted under three tableting pressures gave the results of the measurements of the hardness and the oral disintegration time under respective tableting pressures shown in FIG. 7. From the measurement results shown in FIG. 7, it was evident that the orally disintegrating tablet of Example 8 was successful in obtaining a hardness corresponding to the tableting pressures. On the other hand, the additive for an orally disintegrating tablet of Comparative Example 15 was not successful in obtaining a sufficient hardness. Also, the orally disintegrating tablet of Comparative Example 16 underwent sticking.

Comparative Example 17

In Comparative Example 17, an orally disintegrating tablet was produced in accordance with Example 1 of Japanese Patent No. 5753661. 25 g of NBD-020 supplied from Shin-Etsu Chemical Co., Ltd. as a low-substituted hydroxypropyl cellulose was dispersed in 350 ml of purified water to obtain a dispersion. Using a fluidized bed granulation device (manufactured by Powrex Corp., Model: MP-01), a fluidized bed granulation was conducted while spraying the dispersion to 475 g of Mannit P supplied from Mitsubishi Shoji Foodtech Co., Ltd. as a D-mannitol. The resultant granulate was regulated in the particle size by sieve No. 22, whereby the orally disintegrating tablet of Comparative Example 17 was obtained. To the additive for an orally disintegrating tablet of Comparative Example 17, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 17 was obtained.

Comparative Example 18

In Comparative Example 18, a low-substituted hydroxypropyl cellulose was changed to NBD-022 supplied from Shin-Etsu Chemical Co., Ltd., and otherwise similarly to Comparative Example 17, the orally disintegrating tablet of Comparative Example 18 was produced.

Using tableting pressures of 6 kN, 9 kN and 12 kN, the orally disintegrating tablets of Comparative Examples 17 and 18 were produced respectively. The orally disintegrating tablets of Comparative Examples 17 and 18 which had been tableted under three tableting pressures gave the results of the measurements of the hardness and the oral disintegration time under respective tableting pressures shown in FIG. 8. From the measurement results shown in FIG. 8, it was evident that the orally disintegrating tablet of Comparative Example 17 was not successful in obtaining a sufficient hardness and a short oral disintegration time. Also as evident from the results of Comparative Example 18, only a change in the grade of the low-substituted hydroxypropyl cellulose was not successful in obtaining a sufficient hardness of the orally disintegrating tablet. Accordingly, it is required to investigate various additives described above.

(Comparison with Prior Art Premix Additives)

Prior art premix additives were used to produce orally disintegrating tablets, which were compared.

Comparative Example 19

As an additive for an orally disintegrating tablet of Comparative Example 19, GRANFILLER-D (Registered Trademark) supplied from DAICEL FINECHEM LTD was used to produce an orally disintegrating tablet. To 500 g of the additive for an orally disintegrating tablet of Comparative Example 19, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 19 was obtained.

Comparative Example 20

As an additive for an orally disintegrating tablet of Comparative Example 20, Pharmaburst (Registered Trademark) supplied from SPI Pharma was used to produce an orally disintegrating tablet. To 500 g of the additive for an orally disintegrating tablet of Comparative Example 20, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 20 was obtained.

Comparative Example 21

As an additive for an orally disintegrating tablet of Comparative Example 21, Smart EX (Registered Trademark) supplied from Powrex Corp was used to produce an orally disintegrating tablet. To 500 g of the additive for an orally disintegrating tablet of Comparative Example 21, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 21 was obtained.

Comparative Example 22

As an additive for an orally disintegrating tablet of Comparative Example 22, Parteck (Registered Trademark) ODT supplied from Merck was used to produce an orally disintegrating tablet. To 500 g of the additive for an orally disintegrating tablet of Comparative Example 22, 5 g of a magnesium stearate (Taihei Chemical Industrial Co., Ltd.) was mixed to obtain a pre-tableting powder. Using a tableting machine (VELA5, manufactured by KIKUSUI SEISAKUSHO LTD.), the pre-tableting powder was tableted into tablets each weighing 200 mg, whereby the oral disintegrating tablet of Comparative Example 22 was obtained.

Using tableting pressures of 6 kN, 9 kN and 12 kN, the orally disintegrating tablets of Example 12 and Comparative Examples 19 to 22 were produced respectively. The orally disintegrating tablets of Example 12 and Comparative Examples 19 to 22 which had been tableted under three tableting pressures gave the results of the measurements of the hardness and the oral disintegration time under respective tableting pressures shown in FIG. 9. From the measurement results shown in FIG. 9, it was evident that the orally disintegrating tablet of Example 12 exhibited a sufficient hardness and a short disintegration time of 30 seconds or less when compared with the orally disintegrating tablets of Comparative Examples 21 to 22. The orally disintegrating tablet of Example 12 also exhibited a sufficient hardness equivalent or superior to that of the orally disintegrating tablets of Comparative Examples 19 to 20 as well as an excellent disintegrability.

(Evaluation of Moisture Resistance)

Using a tableting pressure of 9 kN, the orally disintegrating tablets of Example 8 and Comparative Examples 19 to 20 were produced. The orally disintegrating tablets of Example 8 and Comparative Examples 19 to 20 were stored at 25° C. under a humidity of 75% for 1 week, and the difference in the thickness and the hardness of the orally disintegrating tablets between the values before and after the storage was evaluated. FIG. 10 shows the levels of the difference in the thickness and the hardness of the orally disintegrating tablets of Example 8 and Comparative Examples 19 to 20 between the values before and after the storage.

From the results shown in FIG. 10, the orally disintegrating tablets of Comparative Examples 19 and 20 exhibited a substantial increase in the thickness and a substantial reduction in the hardness when stored under the moisturized condition. On the other hand, the orally disintegrating tablet of Example 8 exhibited an increase in the thickness and a reduction in the hardness after storage which were inhibited substantially when compared with the orally disintegrating tablets of Comparative Example 19 and 20. As shown in FIG. 9, the orally disintegrating tablet of Example 8 exhibited a hardness and an oral disintegration time which are equivalent or superior to those of the orally disintegrating tablets of Comparative Examples 19 and 20, and it became also evident that the orally disintegrating tablet of Example 8 was capable of provide an orally disintegrating tablet whose moisture resistance is also excellent.

According to one embodiment of the present invention, a novel additive for an orally disintegrating tablet which imparts a rapid disintegration property and a tablet hardness to the orally disintegrating tablet and a method for producing the same are provided.

What is claimed is:

1. An additive for an orally disintegrating tablet consisting of:
   a D-mannitol;
   a low-substituted hydroxypropyl cellulose having a substitution degree of hydroxypropoxy groups of 8% to 11%;
   a crospovidone; and
   a microcrystalline cellulose,
   wherein the low-substituted hydroxypropyl cellulose excludes:
      a low-substituted hydroxypropyl cellulose having a mean particle size, as determined by a laser diffraction method, of 20 μm or less and a substitution degree of the hydroxypropoxy groups of 11%;
      a low-substituted hydroxypropyl cellulose having a mean particle size, as determined by the laser diffraction method, of 45 μm or less and a substitution degree of the hydroxypropoxy groups of 14%; and
      a low-substituted hydroxypropyl cellulose having a mean particle size, as determined by the laser diffraction method, of 45 μm or less and a substitution degree of the hydroxypropoxy groups of 11% together with a 90% cumulated particle size, as determined by the laser diffraction method, of 100 μm or less.

2. The additive for the orally disintegrating tablet according to claim 1 wherein the D-mannitol has a mean particle size, as determined by the laser diffraction method, of 50 μm or less.

3. The additive for the orally disintegrating tablet according to claim 1 wherein the crospovidone has a mean particle size, as determined by the laser diffraction method, of 100 μm or less.

4. The additive for the orally disintegrating tablet according to claim 2 wherein the crospovidone has a mean particle size, as determined by the laser diffraction method, of 100 μm or less.

5. The additive for the orally disintegrating tablet according to claim 1 wherein the microcrystalline cellulose has a bulk density of 0.22 g/cm$^3$ or more, and
   the bulk density is determined by measuring a mass of a known volume of powder of the microcrystalline cellulose that has been passed through a volumeter into a cup described in a section of the microcrystalline cellulose in Japanese Pharmacopoeia 16th Edition.

6. The additive for the orally disintegrating tablet according to claim 2 wherein the microcrystalline cellulose has a bulk density of 0.22 g/cm$^3$ or more, and
   the bulk density is determined by measuring a mass of a known volume of powder of the microcrystalline cellulose that has been passed through a volumeter into a cup described in a section of the microcrystalline cellulose in Japanese Pharmacopoeia 16th Edition.

7. The additive for the orally disintegrating tablet according to claim 3 wherein the microcrystalline cellulose has a bulk density of 0.22 g/cm$^3$ or more, and
   the bulk density is determined by measuring a mass of a known volume of powder of the microcrystalline cellulose that has been passed through a volumeter into a cup described in a section of the microcrystalline cellulose in Japanese Pharmacopoeia 16th Edition.

8. The additive for the orally disintegrating tablet according to claim 4 wherein the microcrystalline cellulose has a bulk density of 0.22 g/cm$^3$ or more, and
   the bulk density is determined by measuring a mass of a known volume of powder of the microcrystalline cellulose that has been passed through a volumeter into a cup described in a section of the microcrystalline cellulose in Japanese Pharmacopoeia 16th Edition.

9. An orally disintegrating tablet comprising: the additive for the orally disintegrating tablet according to claim 1; and a pharmaceutically active ingredient.

10. The orally disintegrating tablet according to claim 9 wherein the D-mannitol has a mean particle size, as determined by the laser diffraction method, of 50 μm or less.

11. The orally disintegrating tablet according to claim 9 wherein the crospovidone has a mean particle size, as determined by the laser diffraction method, of 100 μm or less.

12. The orally disintegrating tablet according to claim 9 wherein the crystalline cellulose has a bulk density of 0.22 g/cm$^3$ or more, and
   the bulk density is determined by measuring a mass of a known volume of powder of the microcrystalline cellulose that has been passed through a volumeter into a cup described in a section of the microcrystalline cellulose in Japanese Pharmacopoeia 16th Edition.

13. A method for producing an additive for an orally disintegrating tablet comprising:
dispersing a low-substituted hydroxypropyl cellulose having a substitution degree of a hydroxypropoxy groups of 8% to 11% in water to prepare a dispersion; and
performing granulation by spraying the dispersion to a mixture consisting of:
a D-mannitol;
a crospovidone; and
a microcrystalline cellulose,
wherein the low-substituted hydroxypropyl cellulose excludes:
a low-substituted hydroxypropyl cellulose having a mean particle size, as determined by a laser diffraction method, of 20 µm or less and a substitution degree of the hydroxypropoxy groups of 11%;
a low-substituted hydroxypropyl cellulose having a mean particle size, as determined by the laser diffraction method, of 45 µm or less and a substitution degree of the hydroxypropoxy groups of 14%; and
a low-substituted hydroxypropyl cellulose having a mean particle size, as determined by the laser diffraction method, of 45 µm or less and a substitution degree of the hydroxypropoxy groups of 11% together with a 90% cumulated particle size, as determined by the laser diffraction method, of 100 µm or less.

14. The method for producing the additive for the orally disintegrating tablet according to claim 13 wherein the D-mannitol has a mean particle size, as determined by the laser diffraction method, of 50 µm or less.

15. The method for producing the additive for the orally disintegrating tablet according to claim 13 wherein the crospovidone has a mean particle size, as determined by the laser diffraction method, of 100 µm or less.

16. The method for producing the additive for the orally disintegrating tablet according to claim 14 wherein the crospovidone has a mean particle size, as determined by the laser diffraction method, of 100 µm or less.

17. The method for producing the additive for the orally disintegrating tablet according to claim 13 wherein the microcrystalline cellulose has a bulk density of 0.22 g/cm$^3$ or more, and
the bulk density is determined by measuring a mass of a known volume of powder of the microcrystalline cellulose that has been passed through a volumeter into a cup described in a section of the microcrystalline cellulose in Japanese Pharmacopoeia 16th Edition.

* * * * *